US00PP14866P2

(12) United States Plant Patent
Hummel

(10) Patent No.: US PP14,866 P2
(45) Date of Patent: Jun. 8, 2004

(54) HEBE PLANT NAMED 'CHAMPSEIONT'

(50) Latin Name: *Hebe hybrida*
Varietal Denomination: Champseiont

(75) Inventor: Adam Hummel, Gwynedd (GB)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 10/437,939

(22) Filed: May 13, 2003

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database 2001/05, Feb. 6, 2001, GTI Jouve Retrieval Software, Citation for 'Champseiont'.*

* cited by examiner

*Primary Examiner*—Annette H Para
(74) *Attorney, Agent, or Firm*—C. A. Whealy

(57) ABSTRACT

A distinct cultivar of Hebe plant named 'Champseiont', characterized by its compact, upright and somewhat outwardly spreading plant form; freely branching growth habit; and small dark green-colored foliage that becomes purple in color during the winter.

1 Drawing Sheet

Botanical classification/cultivar designation: *Hebe hybrida* cultivar Champseiont.

BACKGROUND OF THE INVENTION

The present Invention relates to a new and distinct cultivar of Hebe plant, botanically known as *Hebe hybrida*, and hereinafter referred to by the name 'Champseiont'.

The new Hebe was discovered by the Inventor in 1995 in a controlled environment in Gwynedd, United Kingdom, as a naturally-occurring whole plant mutation of the *Hebe hybrida* cultivar Autumn Glory, not patented. The new Hebe was selected by the Inventor on the basis of its small dark green-colored leaves.

Asexual reproduction of the new Hebe by cuttings in a controlled environment in Gwynedd, United Kingdom, since 1995, has shown that the unique features of this new Hebe are stable and reproduced true to type in successive generations.

SUMMARY OF THE INVENTION

Plants of the cultivar Champseiont have not been observed under all possible environmental conditions. The phenotype may vary somewhat with variations in environment such as temperature and light intensity without, however, any variance in genotype.

The following traits have been repeatedly observed and are determined to be the unique characteristics of 'Champseiont'. These characteristics in combination distinguish 'Champseiont' as a new and distinct cultivar:

1. Compact, upright and somewhat outwardly spreading plant form.
2. Freely branching growth habit.
3. Small dark green-colored foliage that becomes purple in color during the winter.

Plants of the cultivar Champseiont are most similar to plants of the parent, the cultivar Autumn Glory. However, in side-by-side comparisons conducted in Gwynedd, United Kingdom, plants of the new Hebe differed from plants of the cultivar Autumn Glory in the following characteristics:

1. Plants of the new Hebe had smaller leaves than plants of the cultivar Autumn Glory.
2. Plants of the new Hebe had darker green-colored leaves than plants of the cultivar Autumn Glory.
3. Plants of the new Hebe were more resistant to pathogens common to Hebe than plants of the cultivar Autumn Glory.

BRIEF DESCRIPTION OF THE PHOTOGRAPHS

The accompanying colored photographs illustrate the overall appearance of the new Hebe, showing the colors as true as it is reasonably possible to obtain in colored reproductions of this type. Colors in the photographs may differ slightly from the color values cited in the detailed botanical description which accurately describe the colors of the new Hebe.

The photograph at the top of the sheet comprises a side perspective view of a typical plant of 'Champseiont' grown in a container.

The photographs at the bottom of the sheet are close-up views of typical leaves of 'Champseiont'.

DETAILED BOTANICAL DESCRIPTION

In the following description, color references are made to The Royal Horticultural Society Colour Chart, 2001 Edition, except where general terms of ordinary dictionary significance are used. Plants used for the photographs and the following description were about one year old and grown under outdoor field conditions which closely approximate commercial production conditions in Boskoop, The Netherlands. During the production of the plants, day temperatures ranged from 6 to 15° C. and night temperatures ranged from 2 to 8° C. The photographs and description were taken in March, 2003.

Botanical classification: *Hebe hybrida* cultivar Champseiont.

Parentage: Naturally-occurring whole plant mutation of the *Hebe hybrida* cultivar Autumn Glory, not patented.

Propagation:

*Type.*—By cuttings.

*Time to initiate roots.*—Summer: About 14 days at 25° C. Winter: About 70 days at 15° C.

*Time to produce a rooted cutting.*—Summer: About 120 days at 25° C. Winter: About 240 days at 25° C.

*Root description.*—Fibrous.

Plant description:

*Form.*—Evergreen shrub; compact, upright, somewhat outwardly spreading and flattened globular plant form; moderately vigorous growth habit.

*Plant height.*—About 15 cm.

*Plant diameter.*—About 13 cm.

*Lateral branches.*—Quantity per plant: About ten; pinching is not required, but will improve branching. Length: About 6.7 cm. Diameter: About 1.5 mm. Internode length: About 7 mm. Strength: Moderately strong. Texture: Smooth, glabrous; glossy. Color: 187A.

*Foliage description.*—Arrangement: Opposite, simple; sessile. Length: About 1.4 cm. Width: About 0.7 mm. Shape: Obovate. Apex: Mucronulate. Base: Cuneate. Margin: Entire. Texture, upper and lower surfaces: Somewhat leathery, thick; smooth, glabrous; glossy. Venation pattern: Pinnate. Color: Developing foliage, upper surface: 137A. Developing foliage, lower surface: N186C; towards the apex, 147A. Fully expanded foliage, upper surface: Between 137A and 139A; color becoming more purple, close to 187A to N186C during the winter. Fully expanded foliage, lower surface: 137B to 137C; towards the base, 187A. Venation, upper surface: Midrib, 138A; lateral veins not visible. Venation, lower surface: Midrib, 183C; lateral veins not visible.

Flower description: Flower development has not been observed.

Disease/pest resistance: Plants of the new Hebe have not been noted to be resistant to pathogens and pests common to Hebe.

Temperature tolerance: Plants of the new Hebe are hardy to U.S.D.A. Zone 8 and have been observed to tolerate temperatures as high as 35° C.

It is claimed:

1. A new and distinct cultivar of Hebe plant named 'Champseiont', as illustrated and described.

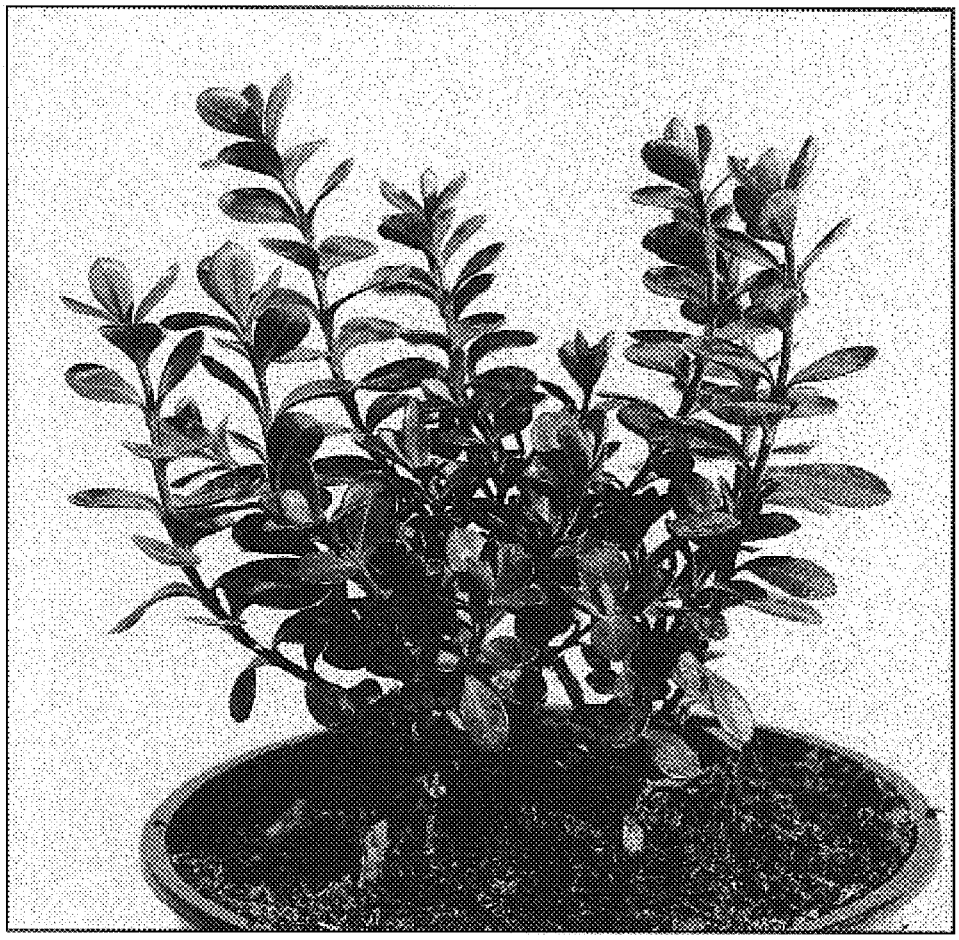
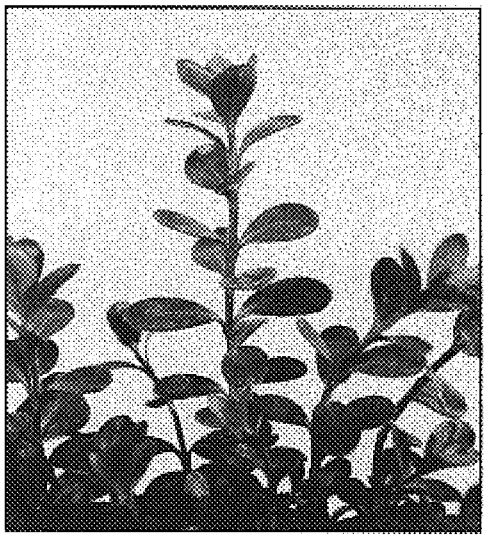
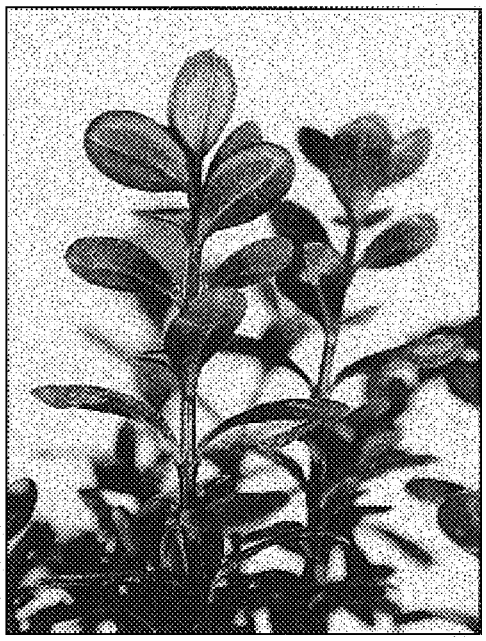

* * * * *